United States Patent
Loyd et al.

(10) Patent No.: US 8,986,272 B2
(45) Date of Patent: Mar. 24, 2015

(54) PACKAGED TAMPON AND APPLICATOR ASSEMBLY

(71) Applicant: Kimberly-Clark Worldwide, Inc., Neenah, WI (US)

(72) Inventors: Adrienne Rae Loyd, Neenah, WI (US); Marcus David Weiher, Sherwood, WI (US); Carrie Nicole Sinkele, Austintown, OH (US); Daniel Thomas LaBash, Appleton, WI (US); Thomas William VanDenBogart, Slinger, WI (US); Gary John Borkowski, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 222 days.

(21) Appl. No.: 13/660,267

(22) Filed: Oct. 25, 2012

(65) Prior Publication Data

US 2013/0053810 A1    Feb. 28, 2013

Related U.S. Application Data

(63) Continuation of application No. 11/321,263, filed on Dec. 29, 2005, now Pat. No. 8,317,765.

(51) Int. Cl.
*A61F 13/15* (2006.01)
*A61F 13/551* (2006.01)
*A61F 15/00* (2006.01)

(52) U.S. Cl.
CPC ....... *A61F 13/5518* (2013.01); *A61F 13/55185* (2013.01); *A61F 15/003* (2013.01)
USPC ............. 604/385.02; 604/385.17; 604/385.18

(58) Field of Classification Search
USPC .............. 604/11, 15, 385.02, 385.17, 385.18; 424/430, 431
See application file for complete search history.

(56) References Cited

U.S. PATENT DOCUMENTS

| | | | |
|---|---|---|---|
| 4,170,305 | A | 10/1979 | Hull, Jr. et al. |
| 4,881,644 | A | 11/1989 | Norquest et al. |
| 6,478,763 | B1 | 11/2002 | Simonsen et al. |
| 6,955,665 | B2 | 10/2005 | Domeier et al. |
| 2003/0220624 | A1 | 11/2003 | Domeier et al. |

FOREIGN PATENT DOCUMENTS

| | | |
|---|---|---|
| EP | 1297805 A2 | 4/2003 |
| WO | 9623711 A | 8/1996 |
| WO | 02067837 A2 | 9/2002 |

OTHER PUBLICATIONS

International Search Report for PCT/US2006/042434 dated Feb. 8, 2007; 4 pages.

*Primary Examiner* — Melanie Hand
(74) *Attorney, Agent, or Firm* — Armstrong Teasdale LLP

(57) ABSTRACT

A package includes a tampon and applicator assembly and a wrapper for enclosing the tampon and applicator assembly. The wrapper is selectively configurable between a sealed configuration wherein the tampon and applicator assembly are sealingly enclosed in the wrapper and an opened configuration for allowing the tampon and applicator assembly to be removed from the wrapper. The wrapper has a front panel, a back panel, two side edges, two end edges, an interior space, a longitudinal axis, and a transverse axis. The front panel has, in the opened configuration of the wrapper, a pair of spaced-apart longitudinal components extending generally parallel to each other and longitudinally of the wrapper to define an opening in the wrapper. Each of the longitudinal components is spaced inward from the respective side edge.

20 Claims, 11 Drawing Sheets

PACKAGED TAMPON AND APPLICATOR ASSEMBLY

CROSS-REFERENCE TO RELATED APPLICATION

This application is a continuation of U.S. patent application Ser. No. 11/321,263 filed Dec. 29, 2005, which is hereby incorporated by reference in its entirety.

BACKGROUND

The present invention relates generally to tampon and applicator assemblies, and more particularly to the individual packaging of a tampon and applicator assembly.

Vaginal tampons are disposable absorbent articles sized and shaped (e.g., cylindrical) for insertion into a women's vagina for absorption of body fluids generally discharged during the woman's menstrual period. Insertion of the tampon into the vagina is commonly achieved using a tampon applicator that comes initially assembled with the tampon. The applicator, which is often made of plastic or cardboard, is disposable. Thus, after the applicator has been used to insert the tampon into the user's vagina the applicator is discarded.

Typically, a single tampon and applicator assembly are packaged together as an individual unit in a disposable wrapper to maintain both the tampon and the applicator in a hygienic condition. Thus, before the tampon and applicator assembly can be used, it must be removed from the wrapper. Conventionally, tampon wrappers are provided with a serrated edge, e.g., having numerous peaks and valleys. The valleys of the serrated edge provide multiple tearing points for use in tearing open the wrapper. One drawback to this approach is that it often leads to small pieces of the wrapper being separated from the wrapper at the serrated edge. As a result, the user must often make multiple tears in order to open the wrapper sufficiently to remove the tampon and applicator assembly, which is frustrating to the user and creates small pieces of wrapper that are difficult to manage (i.e., inconvenient to pick up and throw away).

Another known wrapper construction provides a tear strip in the wrapper, typically extending the length of the wrapper. A tab may be attached to the tear strip at its edge so that it can be grasped by the user. In use, a woman grasps the tab and pulls the tab in the direction of the tear strip thereby creating an opening in the wrapper through which the tampon and applicator assembly is removed. The tear strip may also be engaged by tearing a serrated edge in the absence of a tab. Often, the tear strip extends the length of the wrapper. Thus, tearing the tear strip from the wrapper completely tears open the wrapper along its length. As a result, the tampon applicator and wrapper are commonly disposed of separately. Moreover, the tabs can sometimes be difficult to grasp, making it hard to open this type of wrapper.

There is a need, therefore, for a packaged tampon and applicator assembly that facilitates opening of the wrapper while maintaining the ability of the wrapper to be subsequently used to hygienically wrap and discard the used tampon applicator.

SUMMARY

In one aspect, a package generally comprises a tampon and applicator assembly and a wrapper for enclosing the tampon and applicator assembly. The tampon and applicator assembly comprises a tampon and an applicator assembled together with the tampon and adapted to facilitate insertion of the tampon in a user. The wrapper is selectively configurable between a sealed configuration wherein the tampon and applicator assembly are sealingly enclosed in the wrapper and an opened configuration for allowing the tampon and applicator assembly to be removed from the wrapper. The wrapper has a front panel, a back panel, two side edges, two end edges, an interior space, a longitudinal axis, and a transverse axis. The front panel has, in the opened configuration of the wrapper, a pair of spaced-apart longitudinal components extending generally parallel to each other and longitudinally of the wrapper to define an opening in the wrapper. Each of the longitudinal components is spaced inward from the respective side edge.

In another aspect, a package generally comprises a tampon and applicator assembly and a wrapper for enclosing the tampon and applicator assembly. The tampon and applicator assembly comprises a tampon and an applicator assembled together with the tampon and adapted to facilitate insertion of the tampon in a user. The applicator includes a gripping portion and an insertion portion. The wrapper is selectively configurable between a sealed configuration wherein the tampon and applicator assembly are sealingly enclosed in the wrapper and an opened configuration for allowing the tampon and applicator assembly to be removed from the wrapper. The wrapper has a front panel, a back panel, two side edges, two end edges, an interior space, a longitudinal axis, and a transverse axis. The front panel, in the opened configuration of the wrapper, has an opening therein for exposing the gripping portion of the applicator. The insertion portion of the applicator is unexposed in the opened configuration of the wrapper until the user removes the tampon and applicator assembly from the wrapper.

In yet another aspect, a package generally comprises a tampon and applicator assembly and a wrapper for enclosing the tampon and applicator assembly. The tampon and applicator assembly comprises a tampon and an applicator assembled together with the tampon and adapted to facilitate insertion of the tampon in a user. The wrapper is selectively configurable between a sealed configuration wherein the tampon and applicator assembly are sealingly enclosed in the wrapper and an opened configuration for allowing the tampon and applicator assembly to be removed from the wrapper. The wrapper has a front panel, a back panel, two side edges, two end edges, an interior space, a longitudinal axis, and a transverse axis. The front panel has, in the opened configuration of the wrapper, a longitudinal component extending longitudinally of the wrapper and a transverse component extending transversely of the wrapper. The longitudinal and transverse components define an opening in the wrapper. The longitudinal component is spaced inward from the side edges and the transverse component is spaced inward from the end edges.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
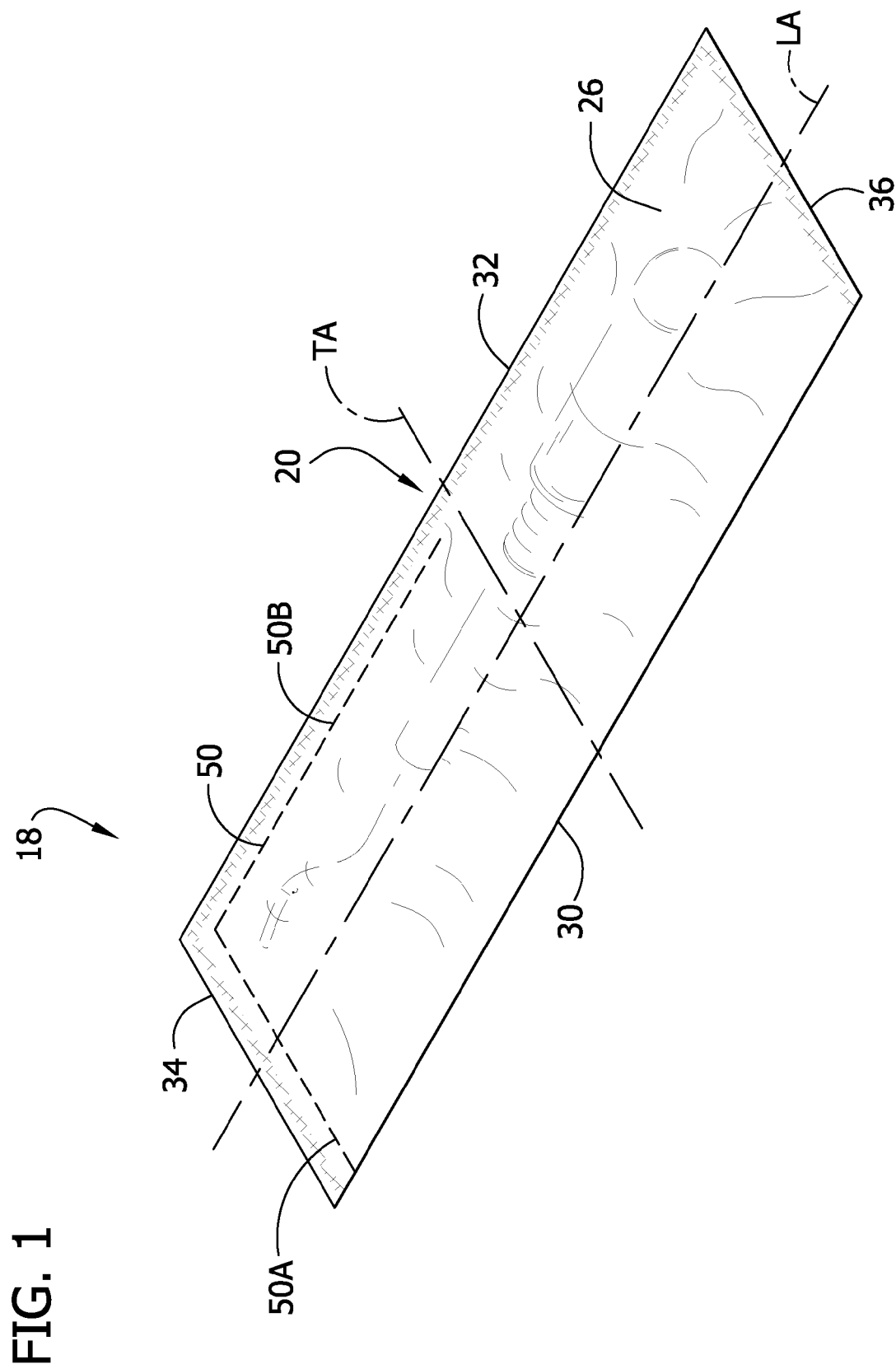
FIG. 1 is a perspective view of one embodiment of packaged tampon and applicator assembly in which the tampon and applicator assembly is sealingly enclosed within a wrapper.
Figure 2:
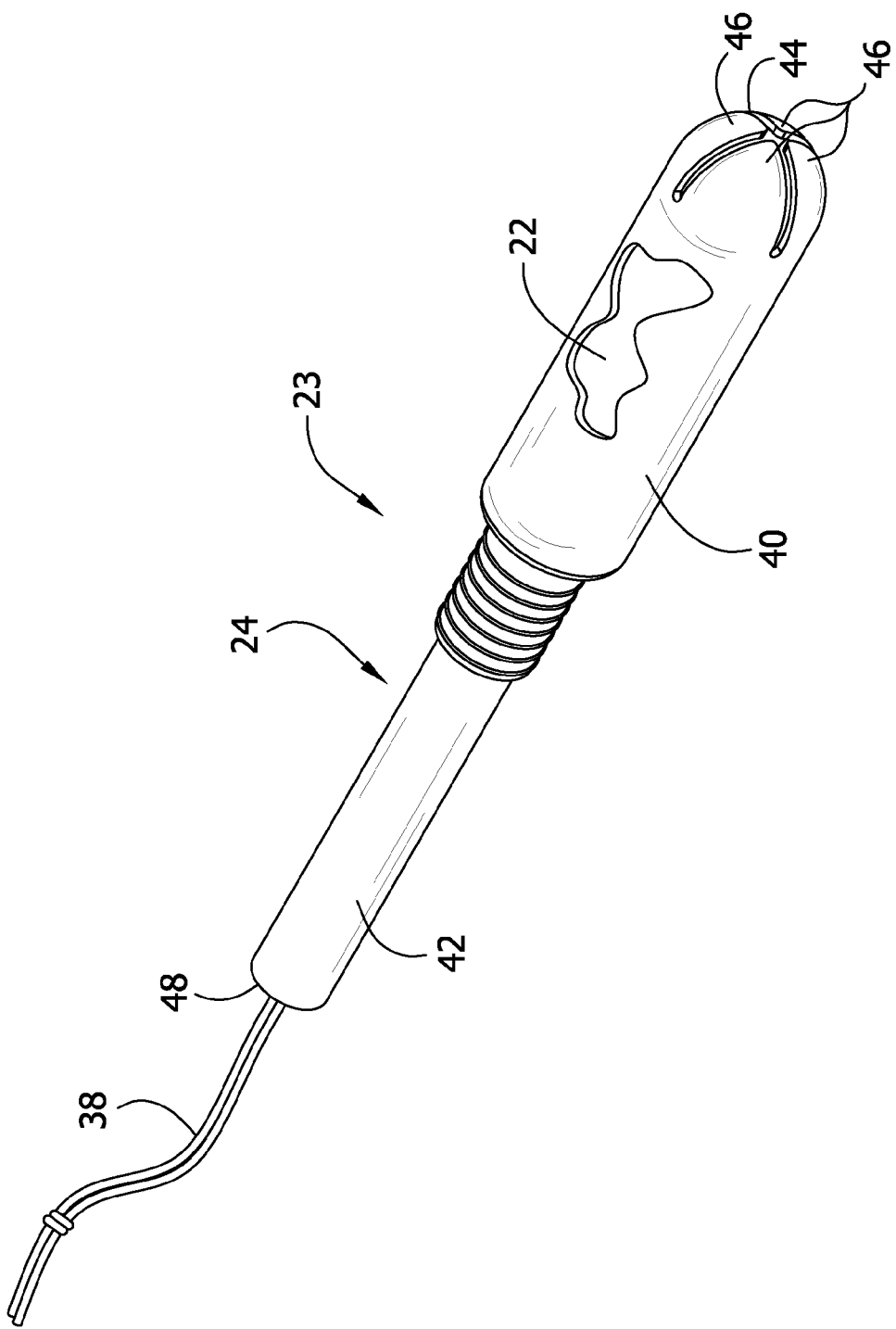
FIG. 2 is a perspective view of a tampon and applicator assembly.
Figure 3:
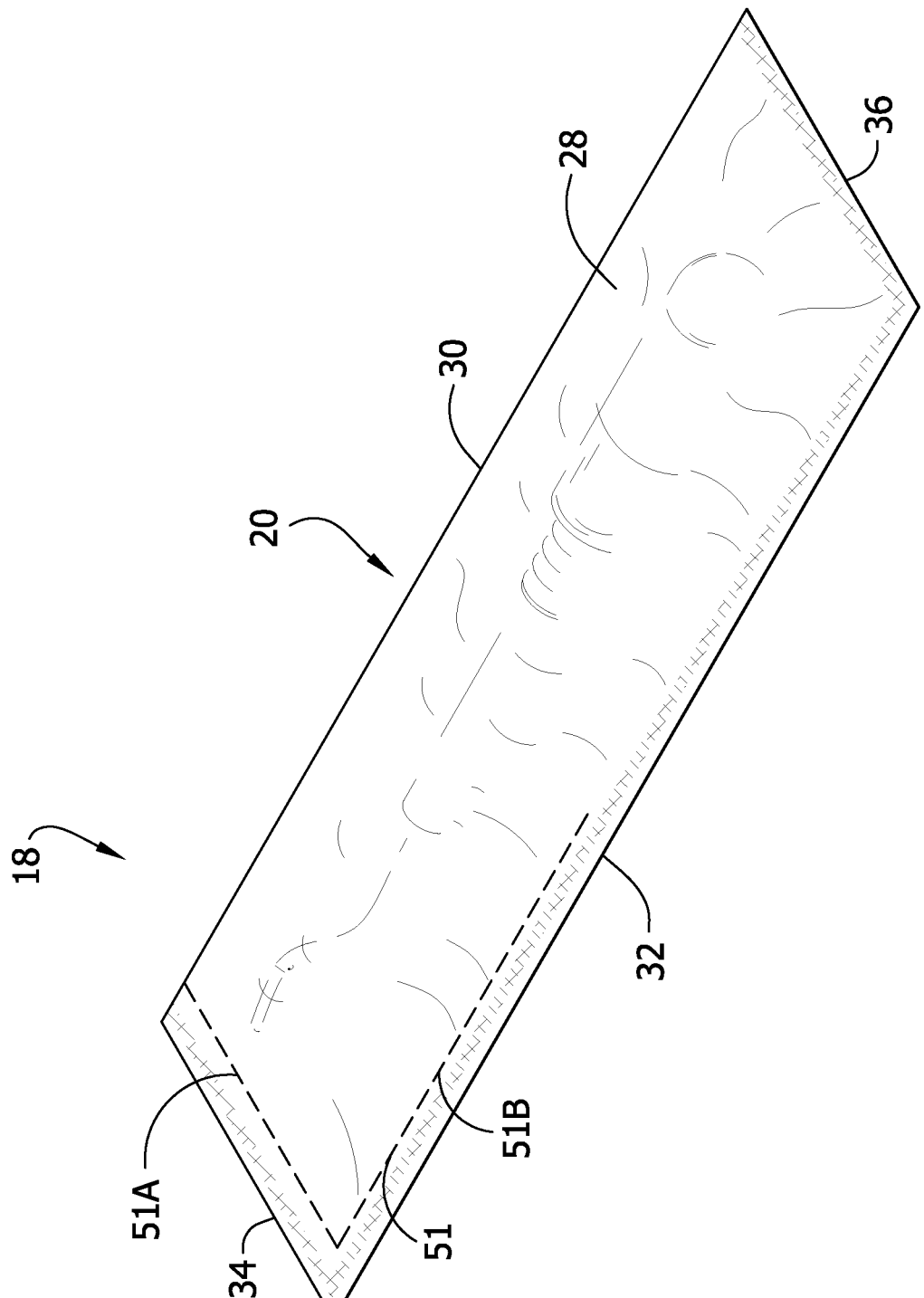
FIG. 3 is a backside perspective of the packaged tampon and applicator assembly of FIG. 1.

Referring now to the drawings and in particular to FIGS. 1-3, one embodiment of packaged tampon and applicator assembly is generally designated by reference numeral 18 and comprises a wrapper, generally designated 20 sealingly enclosing a tampon and applicator assembly, generally designated 23 (FIG. 2). The tampon and applicator assembly 23 suitably comprises a vaginal tampon 22 (hereinafter "tampon") and corresponding applicator, generally designated 24, for use in inserting the tampon into a woman's vagina. It is understood, however, that the packaged tampon and applicator assembly described herein is applicable to other types of tampons such as, without limitation, medical tampons, dental tampons, surgical tampons, nasal tampons, and the like.

The tampon 22 illustrated in FIG. 2 has a cylindrical fibrous body that is sized and shaped for insertion into a women's vagina during her menstrual period to absorb menses, blood, and other body fluid. The tampon 22 includes a withdrawal string 38 that is fastened to the body of the tampon generally adjacent a rearward end thereof. The string 38 is used to pull the tampon 22 from the woman's vagina. The body of the tampon 22 is made of absorbent materials such as absorbent fibers, including natural and synthetic fibers, compressed into a unitary body of a size that may easily be inserted into the vaginal cavity. Suitable fibers include, for example, cellulosic fibers such as cotton and rayon. Fibers may be 100% cotton, 100% rayon, a blend of cotton and rayon, or other materials known to be suitable for tampon use. The body of the tampon 22 has an elongated cylindrical shape so that it has a sufficiently large body of absorbent material to provide the required absorbing capacity. It is understood that the tampon body can made in a variety of shapes besides cylindrical.

The tampon 22 may also include a cover surrounding the fibrous body. The cover prevents the fibers of the tampon body from directly contacting the inner walls of a woman's vagina. This assures that no fibers will be left behind in the vagina after the tampon 22 is removed. The cover can be tucked into ends of the body of the tampon so as to completely surround and enclose the fibers. The cover can also be constructed from a heat-sealable material to assist in bonding it to the fibers, such as by heat and/or pressure. The cover can be formed from a nonwoven material such as a polyolefin, particularly polypropylene or polyethylene. A suitable material is a spunbond material. Suitable methods and materials for the production of tampons are well known to those skilled in the art.

As illustrated in FIG. 2, the tampon applicator 24, which is used to insert the tampon 22 into a woman's vagina, comprises an outer tube 40 (broadly, "an insertion portion") and an inner tube 42 (broadly, "a gripping portion"). The outer tube 40 is sized and shaped to house the tampon 22. A portion of the outer tube 40 is partially broken away in FIG. 2 to illustrate the tampon 22. In the illustrated embodiment, the outer tube 40 has a substantially smooth exterior surface, which facilitates insertion of the tampon applicator 24, and thus the tampon 22, into a woman's vagina. When the surface of the exterior layer is smooth and/or slippery, the outer tube 40 will easily slide into a woman's vagina without subjecting the internal tissues of the woman's vagina to abrasion. The outer tube 40 may be coated to give it a high slip characteristic. Wax, polyethylene, a combination of wax and polyethylene, cellophane, and clay are representative coatings that can be applied to the exterior layer to facilitate comfortable insertion. The illustrated outer tube 40 is a straight, elongated cylindrical tube. It is understood however that the applicator 24 could have different shapes and sizes than those illustrated and described herein.

Extending outwardly from the outer tube is an insertion tip 44. The insertion tip 44, which is formed as one-piece with the outer tube 40, may be dome-shaped to facilitate insertion of the outer tube into a woman's vagina in a comfortable manner. The illustrated insertion tip 44 is made of a thin, flexible material and has a plurality of soft, flexible petals 46 that are arranged to form the dome-shape. The petals 46 are capable of radially flexing (i.e., bending outward) to provide an enlarged opening through which the tampon 22 can exit when it is pushed forward by the inner tube 42. The outer tube 40 may be formed without the insertion tip 44. Without the insertion tip, the outer tube includes an opened end (not shown) through which the tampon 22 can exit when it is pushed forward by the inner tube.

The inner tube 42 is an elongate cylinder that is used to engage the tampon 22 contained in the outer tube 40. A free end 48 of the inner tube 42 is configured for digital manipulation by the user's forefinger so that the user can move the inner tube with respect to the outer tube 40. In other words, the free end 48 functions as a grip for the forefinger of the user. It is also possible to form an enlarged ring or flange on the distal end of the inner tube 42 to provide for a larger contact surface for the user's forefinger.

The inner tube 42 is used to push the tampon 22 out of the outer tube 40 and into the woman's vagina by telescopically moving into the outer tube. As the inner tube 42 is pushed into the outer tube 40 by the user, the tampon 22 is forced forward against the insertion tip 44. The contact by the tampon 22 causes the petals 46 of the insertion tip 44 to radially open to a diameter sufficient to allow the tampon to exit the outer tube 40 and into the woman's vagina. With the tampon 22 properly positioned in the woman's vagina, the tampon applicator 24 is withdrawn. In a used configuration of the tampon applicator 24, the inner tube 42 is received in the outer tube 40. As a result, the used configuration of the tampon applicator 24 has a length that is substantially equal to a length of the outer tube 40.

The inner tube 42, the outer tube 40, and the insertion tip 44 can be formed from any suitable material including, but not limited to, paper, paperboard, cardboard, plastic, thermoplastic film, or a combination thereof. If paper, paperboard, or cardboard is used, it can be coated with a wax or water-insoluble polymer to render it water-resistant. Suitable plastic materials include polyolefins, such as low density polyethylene and low density polypropylene. Construction and operation of the tampon and tampon applicator described heretofore is conventional and known to those skilled in the art. For example, such a tampon and tampon applicator are available from Kimberly-Clark Global Sales, Inc. under the tradename KOTEX SECURITY.

Referring to FIGS. 1 and 3, the illustrated wrapper 20 suitably has a front panel 26 and a back panel 28 sealingly engaged with the front panel to define an interior space sized and shaped for receiving the tampon and applicator assembly 23 as initially assembled and unused. Thus, the wrapped assembly 18 can be carried as a single unit by the user (e.g., in a purse, backpack, or a pocket) in a sealed, hygienic condition.

Figure 10:
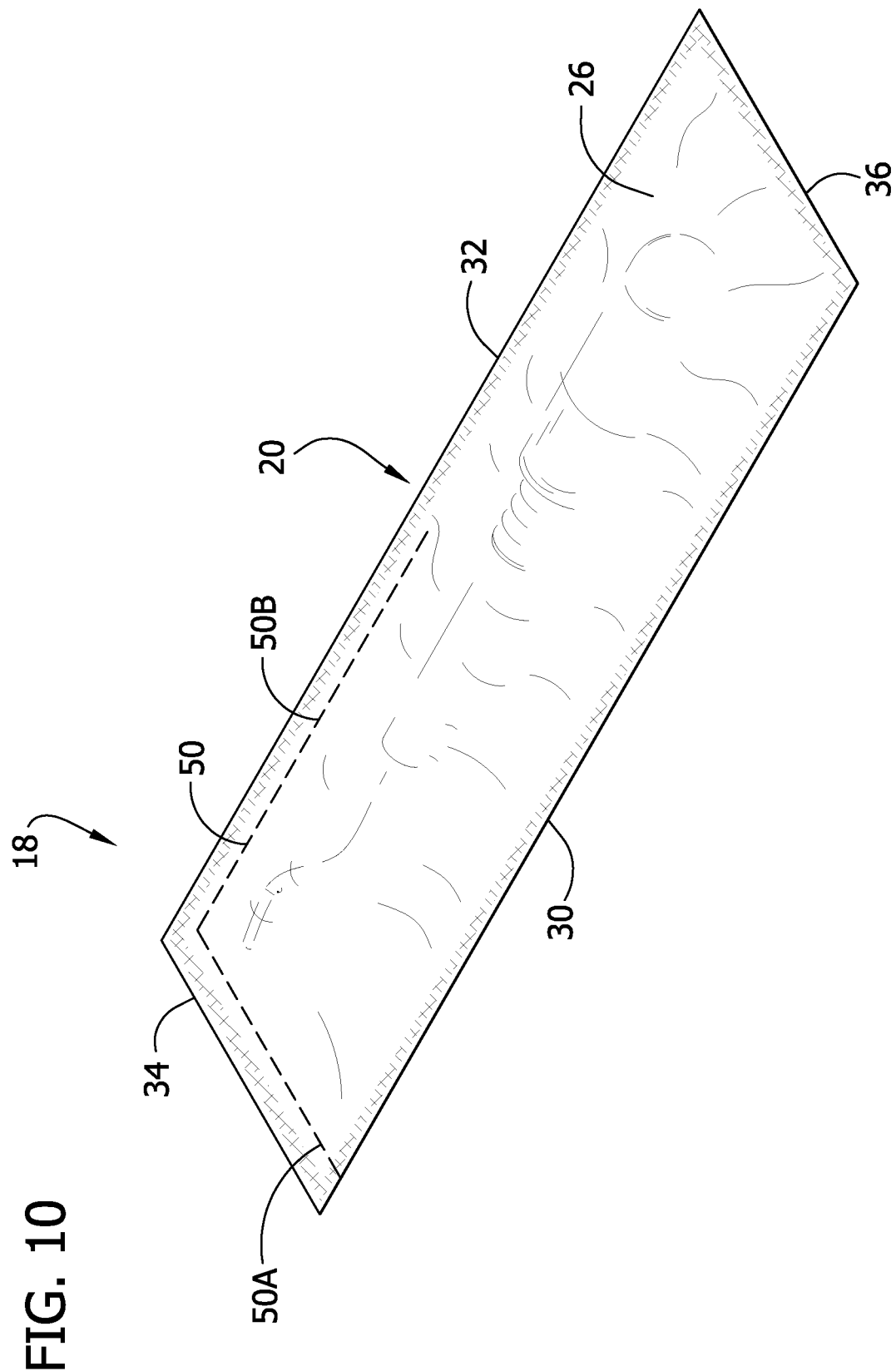
FIG. 10 is a sixth embodiment of a wrapper for a packaged tampon and applicator.

The wrapper 20 illustrated in FIG. 1 comprises two side edges 30, 32, two end edges 34, 36, a longitudinal axis LA, and a transverse axis TA. The wrapper 20 is suitably formed from a single-piece of sheet material that has been folded in half about a longitudinal center line of the sheet. Thus, the fold line forms one of the side edges 30 of the wrapper. The front panel 26 of the wrapper 20 is joined with the back panel 28 of the wrapper along the other side edge 32 and at the end edges 34, 36, such as by heat sealing, to seal the interior space of the wrapper. It is understood, however, that the front panel 26 and back panel 28 of the wrapper 20 may be joined in other ways without departing from the scope of the present invention (e.g., adhesive). It is also understood that the wrapper could be formed from two separate panels that are sealed together along both side edges and the end edges such as is illustrated in FIG. 10. It is further understood that the fold line may be omitted, e.g., the wrapper may be bent but otherwise uncreased without departing from the scope of this invention.

Figure 4:
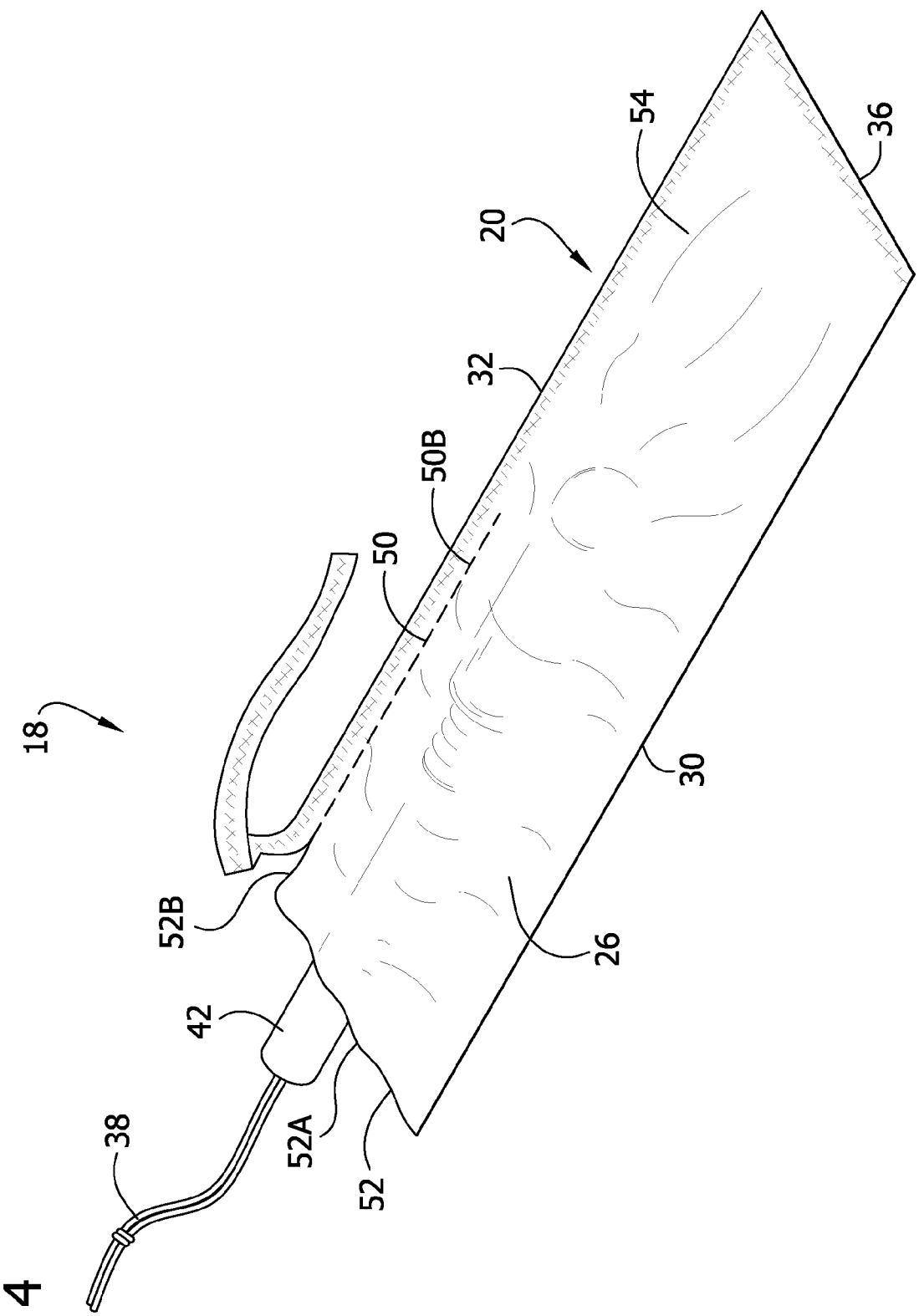
FIG. 4 is a perspective view of the packaged tampon and applicator assembly with the wrapper torn open to permit removal of the tampon and applicator assembly from the wrapper.

In a sealed configuration of the wrapper 20, as illustrated in FIGS. 1 and 3, the tampon and applicator assembly 23 is sealingly enclosed in the wrapper for maintaining the assembly in a hygienic condition. The wrapper 20 can be selectively configured from the sealed configuration to an opened configuration as illustrated in FIG. 4 to permit removal of the tampon 22 and tampon applicator 24 from the wrapper. The tampon 22 and tampon applicator 24 may be arranged in the wrapper 20 so that inner tube 42 can be easily grasped by the user upon altering the wrapper to the opened configuration.

As illustrated in FIGS. 1 and 3, the wrapper 20 suitably has a first line of weakness 50 formed on the front panel 26 of the wrapper and a second line of weakness 51 formed on the back panel 28 of the wrapper. The lines of weakness 50, 51 provide a path along which the wrapper is more readily torn to open the wrapper (i.e., configure to the opened configuration). It is understood that the wrapper may have a line of weakness 50 or 51 disposed on only one of the front and back panels, with the other panel being free of a line of weakness and remain within the scope of this invention.

The lines of weakness 50, 51 suitably comprise a plurality of aligned perforations in the illustrated embodiment. These perforations may be in the form of holes, slits, apertures, voids, or the like, or combinations thereof. The term "line of weakness" is used herein to mean any defined (e.g., intended) structural feature which weakens the wrapper 20 along a predetermined path so that the wrapper 20 is more readily ruptured, or torn, upon application of a tearing force along the line of weakness 50, 51 and is not limited to perforations. For example, in other embodiments the lines of weakness 50, 51 may comprise a plurality of separation points, a score line, a breakaway line or areas, a chain stitch, a thinning of the wrapper material or other suitable line of weakness. The lines of weakness 50, 51 may be suitably formed by partial pressure cutting, partial ultrasonic cutting, partial thermal deformation, mechanical thinning, or other suitable techniques.

The lines of weakness 50, 51 in the illustrated configuration extend generally adjacent (e.g., along the edge margin of) one of the end edges 34 and generally adjacent one of the side edges 32. Thus, the lines of weakness 50, 51 include transverse components 50A, 51A (i.e., the portions of the lines of weakness adjacent the end edge 34) and longitudinal components 50B, 51B (i.e., the portions of the lines of weakness adjacent the side edge 32). The longitudinal components 50B, 51B each have a length that is suitably less than the length of the wrapper 20. For example, in one configuration the longitudinal components 50B, 51B of the lines of weakness 50 may have lengths that are between about 20 percent of the length of the wrapper and about 75 percent of the length of the wrapper. In another configuration the longitudinal components 50B, 51B of the lines of weakness 50, 51 may have lengths that are between about 30 percent of the length of the wrapper and about 60 percent of the length of the wrapper. For example, in the illustrated configuration, the lengths of the lines of weakness 50, 51 is about 50 percent the length of the wrapper 20. While the lines of weakness 50, 51 in the illustrated embodiment are substantially equal in the length, the lengths of the lines of weakness 50, 51 can be different without departing from the scope of this invention. Thus, the line of weakness 50 on the front panel 26 of the wrapper 20 may be longer or shorter than the line of weakness 51 on the back panel 28 of the wrapper.

The lines of weakness 50, 51 provide a path of low resistance along which the wrapper 20 may be torn. However, the level of resistance to tearing provided by the lines of weakness 50, 51 can be altered. For example, increasing the size of the perforations, increasing the number of perforations, and/or decreasing the spacing between the perforations lowers the resistance to tearing along the lines of weakness. Lowering the tear resistance would make the wrapper 20 easier to open. As a result, less force is needed to tear the wrapper 20 along the lines of weakness 50, 51. However, lowering the tear resistance may increase the risk that the wrapper 20 will unintentionally tear apart or tear more than desired. On the other hand, decreasing the size of the perforations, decreasing the number of perforations, and/or increasing the spacing between the perforations would increase the resistance of the lines of weakness 50, 51, thereby requiring a greater force to tear the wrapper 20 along the lines of weakness. In addition, the lines of weakness 50, 51 can have varying tear resistance along their length or a portion of their length. For example, the perforations can be spaced close together along the transverse components 50A, 51A of the lines of weakness while the perforations can be spaced further apart along the longitudinal components 50B, 51B. In this arrangement, the transverse components 50A, 51B of the lines of weakness 50, 51 would be easier to tear than the longitudinal component 50B, 51B. The tear resistance of the line of weakness 50 in the front panel 26 of the wrapper 20 may be equal to or different than the tear resistance of the line of weakness 51 in the back panel 28 of the wrapper.

Figure 5:
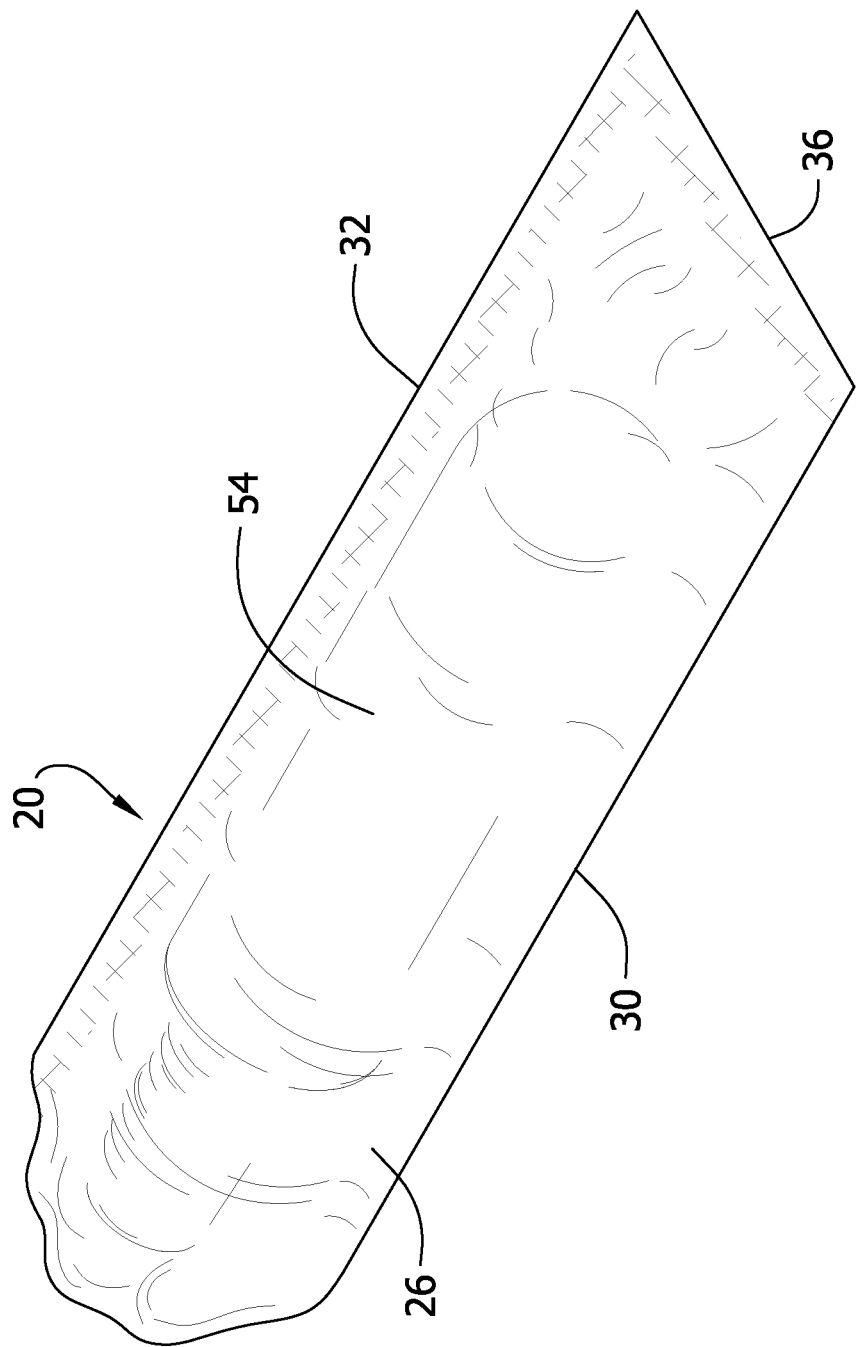
FIG. 5 is an enlarged perspective view of the torn open wrapper enclosing the applicator after it has been used.

In the illustrated embodiment, the tampon and applicator assembly 23 can be accessed by tearing the wrapper 20 along the lines of weakness 50, 51 as illustrated in FIG. 4. Since the lines of weakness 50, 51 define the opening 52, the opening also has a transverse component 52A and a longitudinal component 52B. The longitudinal component 52B of the opening 52 has a length that is suitably between about 20 percent of the length of the wrapper 20 and about 75 percent of the length of the wrapper. In another configuration, the longitudinal component 52B of the opening 52 may have a length that is between about 30 percent of the length of the wrapper and about 60 percent of the length of the wrapper. As an example, in the illustrated configuration the length of the longitudinal component 52B of the opening 52 is about 50 percent of the length of the wrapper 20. As a result, the integrity of about one-half of the wrapper 20 has not been compromised by the opening 52. That is to say that about half of the wrapper 20 remains intact to define an intact portion or pocket 54 after the wrapper has been opened (FIG. 5). Since the lines of weakness 50, 51 do not extend the full length of the wrapper 20, the torn portion of the wrapper remains attached to the pocket 54. Thus, even after it is opened the wrapper 20 remains a single piece. Accordingly, there are no small or separate wrapper pieces that need to be handled and disposed of after the wrapper 20 has been opened.

The length and width of the wrapper 20 is sufficiently oversized relative to the tampon and applicator assembly 23 so that the assembly can be repositioned, either laterally, longitudinally or both, within the wrapper to a position in which the line of weakness 50 in the front panel 26 of the wrapper can be aligned in face-to-face relation with the line of weakness 51 in the back panel 28 of the wrapper free from interposition of the assembly 23 therebetween. In the illustrated configuration, the tampon and applicator assembly 23 can be moved downward and to the left as viewed in FIG. 1. Moving the tampon and applicator assembly 23 to this position allows the lines of weakness 50, 51 in the front panel 26 and back panel 28 of the wrapper 20 to be brought together (e.g., by pinching the wrapper together at the location of the lines of weakness) thereby making it easier to tear the wrapper along both lines of weakness simultaneously.

After having created the opening 52 in the wrapper 20, the tampon and applicator assembly 23 can be removed from the wrapper through the opening. The tampon and applicator assembly 23 can be arranged in the wrapper 20 so that the inner tube 42 is disposed closer to the opened portion of the wrapper than is the outer tube 40. After the tampon 22 has been inserted into the user and there is no longer a use for the tampon applicator 24, the tampon applicator is suitably placed back into the pocket 54 formed by the untorn portion of the wrapper. As shown in FIG. 5, the torn portion of the wrapper 20 above the applicator 24 may be tucked into the pocket 54 to enclose the applicator within the pocket for hygienic handling and discarding of the used applicator. Optionally, the portion of the wrapper 20 above the applicator 24 can be tied together, twisted, or otherwise secured to inhibit the used applicator against unintentionally falling out of the pocket 54. Broadly, the wrapper 20 is thus configured in an applicator disposal configuration (FIG. 5) in which the used applicator 24 is hygienically stored for placement into a waste receptacle or carried in a relatively sealed manner (i.e., the wrapper prevents the applicator from contacting other articles) by the user until a waste receptacle can be found.

In one configuration, the pocket 54 of the wrapper 20 may suitably have a length in the range of about 40 percent greater than a length of the applicator 24 in the used configuration of the applicator to about 20 percent less than the length of the applicator in the used configuration of the applicator. In another configuration, the pocket 54 of the wrapper 20 may have a length in the range of about 15 percent greater than the length of the applicator 24 in the used configuration of the applicator to about 10 percent less than the length of the applicator in the used configuration of the applicator. As an example, in the illustrated configuration the pocket 54 of the wrapper 20 has a length that is approximately equal to that of the applicator 24 in the used configuration of the applicator.

The wrapper 20 may suitably be formed from woven material, non-woven material, films, laminates, or a combination thereof. For example, in one suitable embodiment, the wrapper 20 may be made of paper, polyethylene, polypropylene, oriented polypropylene materials, or the like. In one particularly suitable embodiment, the wrapper 20 is formed of a material that resists tearing beyond the terminal ends of the lines of weakness 50, 51. Suitable examples include, without limitation, a low density polyethylene (LDPE) film; a LDPE/LLDPE (linear low density polyethylene) film laminate; a LDPE/MDPE (medium density polyethylene) film laminate; and a LDPE/HDPE (high density polyethylene) film laminate or the like. One particular material suitable for making the wrapper 20 is available from Pliant Corporation under the tradename XP3-999-1459.0.

Figure 6:
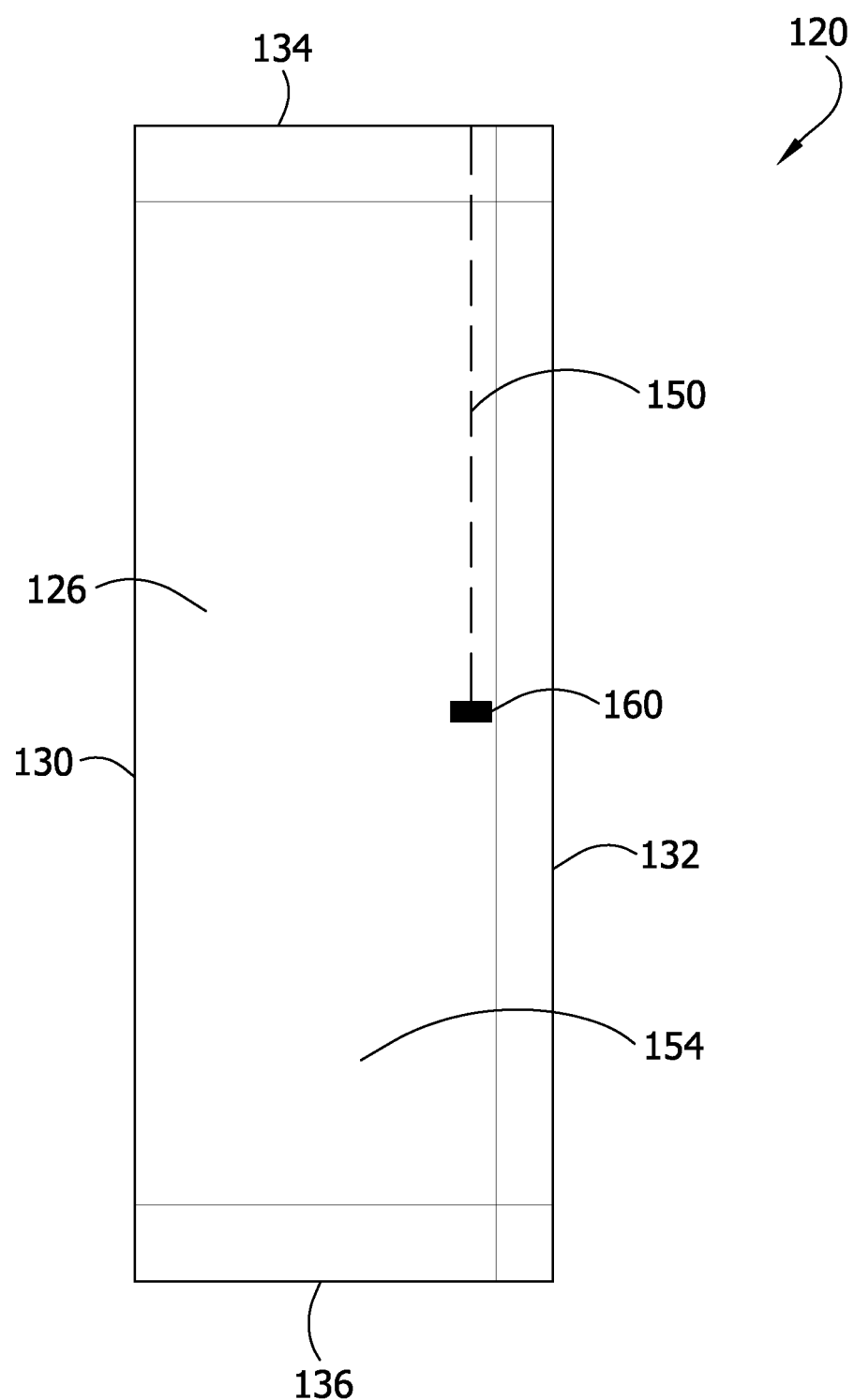
FIG. 6 is a front elevation of a second embodiment of a wrapper for a packaged tampon and applicator assembly.

FIG. 6 illustrates a second embodiment of a wrapper 120 substantially similar to the previous described wrapper 20 except that the lines of weakness (only one line of which is illustrated in FIG. 6 and designated 150, it being understood that a parallel line of weakness is formed in the opposite side of the wrapper) extend only along a side edge 132 of the wrapper. In this configuration, the lines of weakness 150 do not have a transverse component. Moreover, a stop member 160 is positioned adjacent the distal end of each line of weakness 150 to inhibit the wrapper against tearing beyond the ends of the lines of weakness 150. The stop member 160 can be formed by affixing a tab to the wrapper, applying a spot of adhesive to the wrapper, or spot sealing or bonding (e.g., thermal bonding, ultrasonic bonding, pressure bonding) the wrapper. It is understood that other types of stop members could be used without departing from the scope of this invention.

Figure 7:
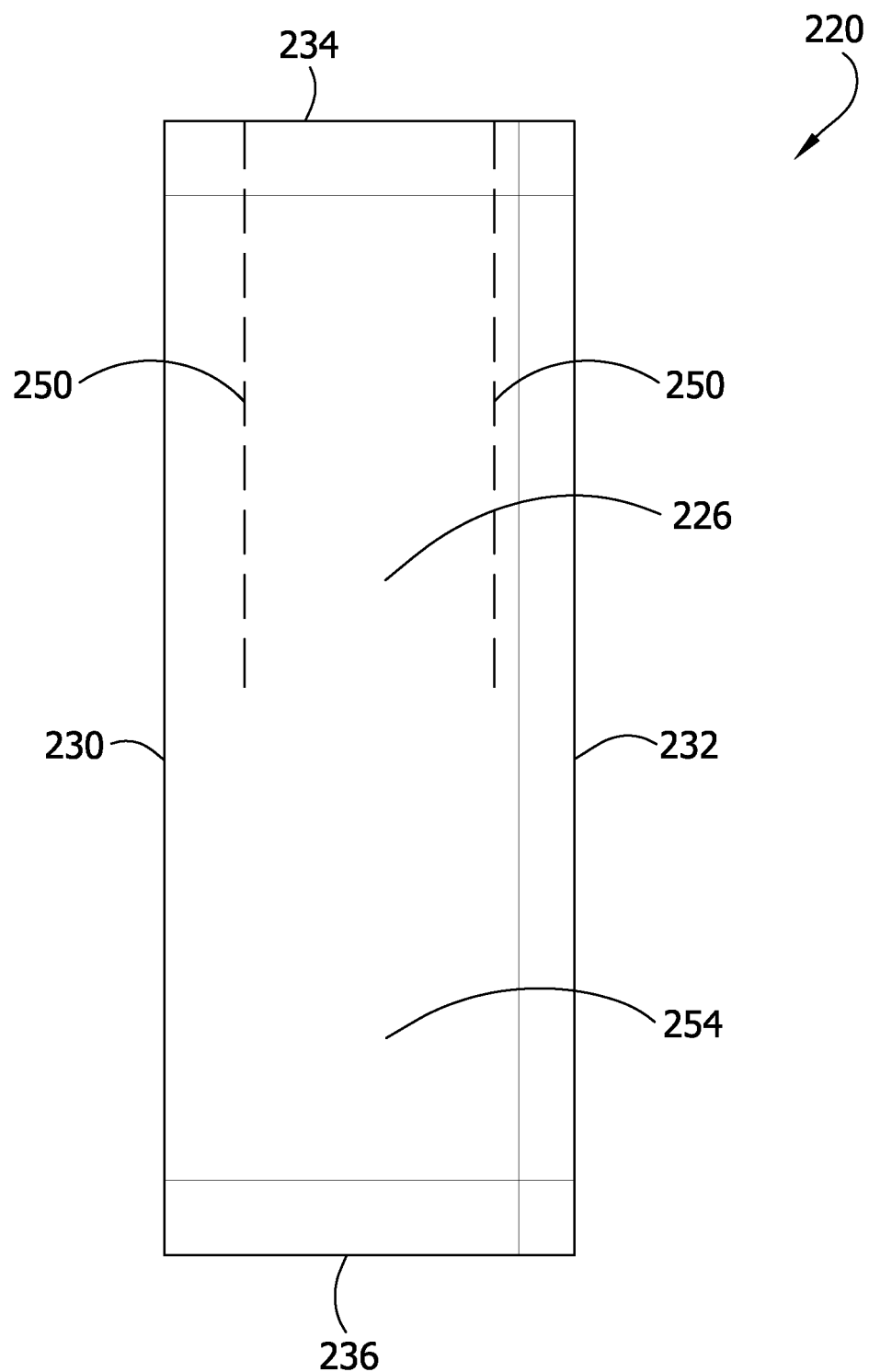
FIG. 7 is a front elevation of a third embodiment of a wrapper for a packaged tampon and applicator assembly.

FIG. 7 illustrates a third embodiment in which a wrapper 220 has two parallel, spaced apart lines of weakness 250 in each of the front and back panels (only the lines of weakness 250 in the front panel being illustrated, it being understood that the lines of weakness in the back panel are parallel to those in the front panel). One line of weakness 250 extends generally adjacent one side edge 230 while the other line of weakness extends generally adjacent the other side edge 232.

Figure 8:
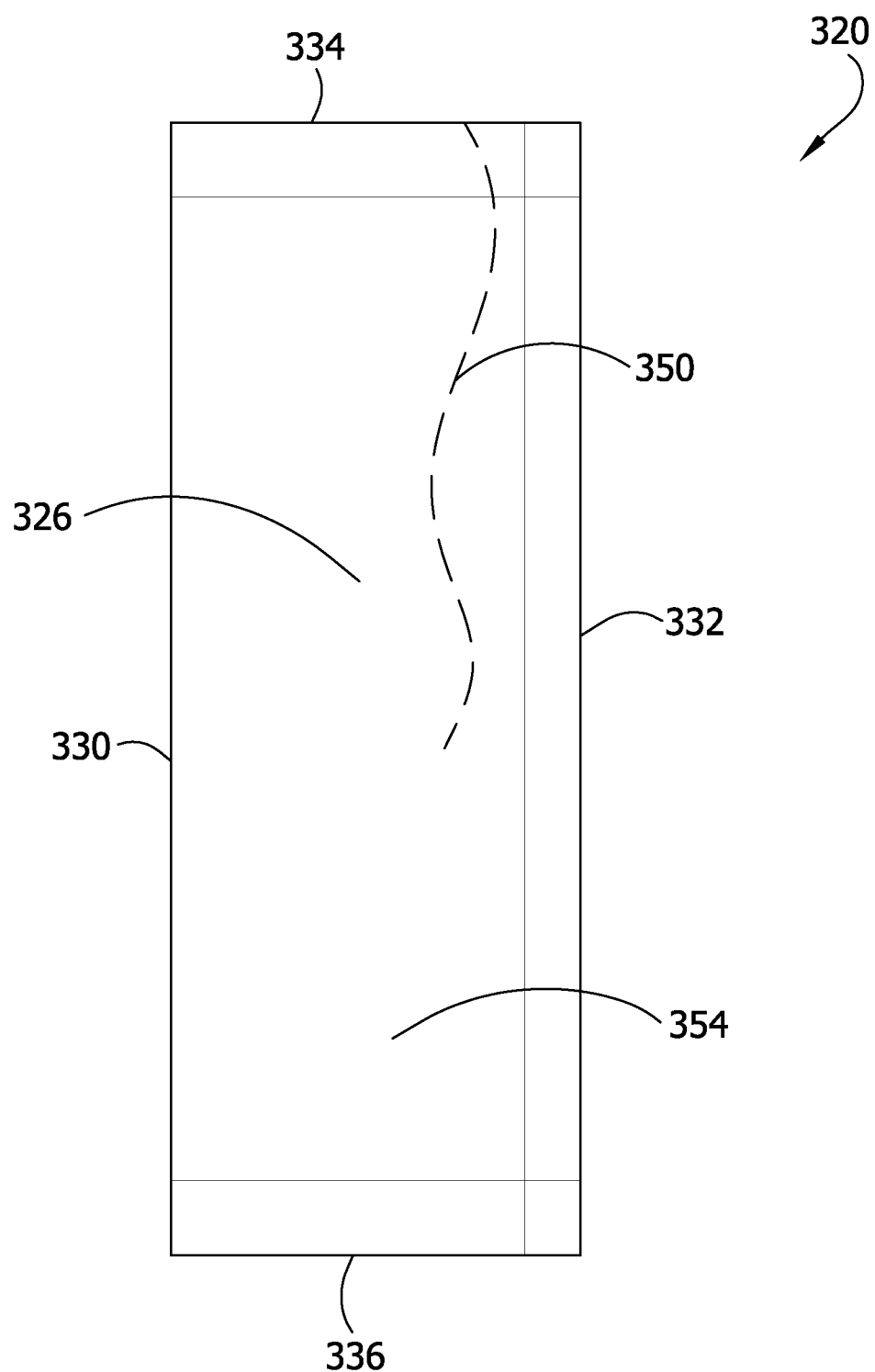
FIG. 8 is a front elevation of a fourth embodiment of a wrapper for a packaged tampon and applicator assembly.
Figure 9:
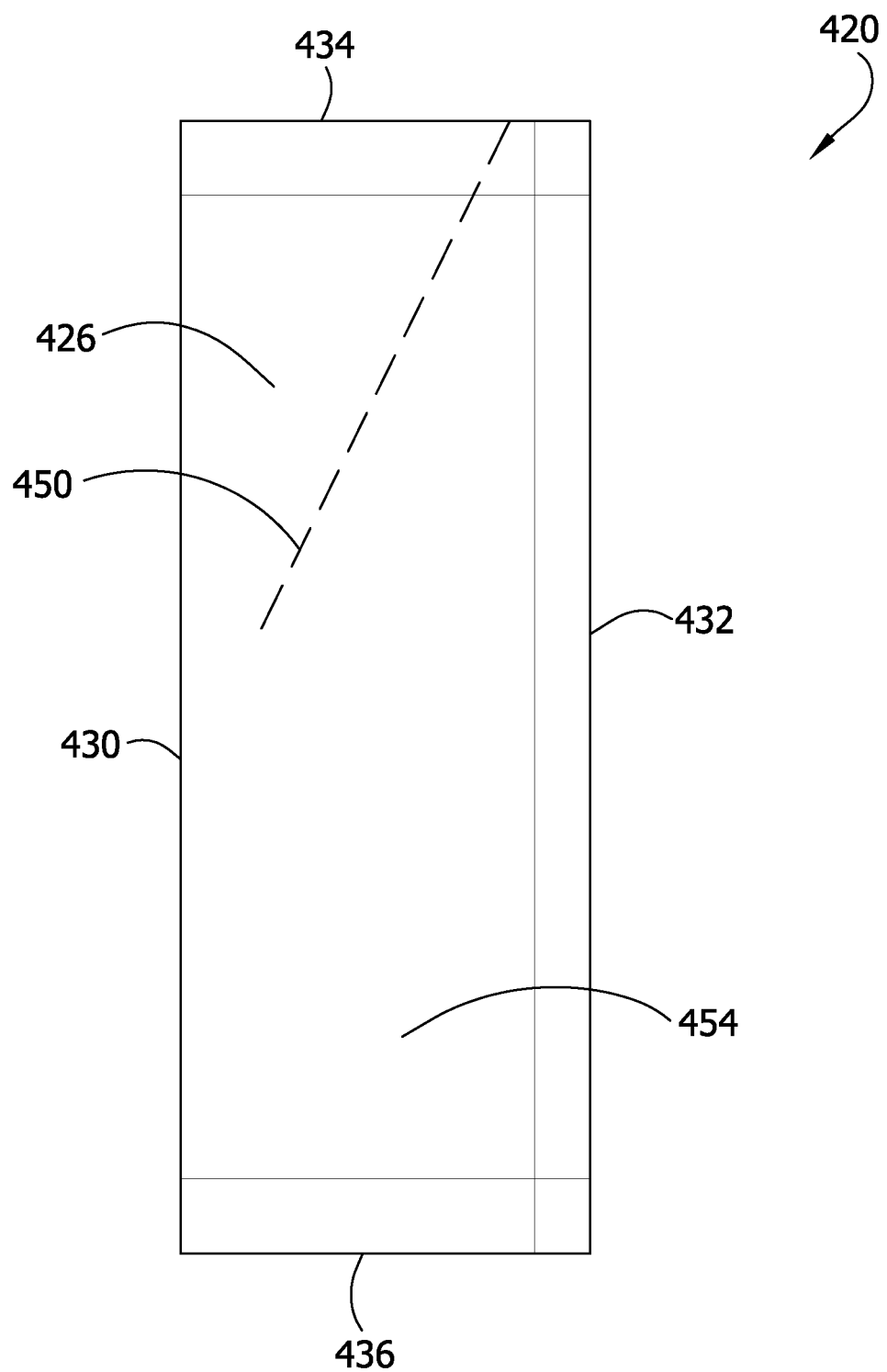
FIG. 9 is a front elevation of a fifth embodiment of a wrapper for a packaged tampon and applicator assembly.

In a fourth embodiment, illustrated in FIG. 8, a wrapper 320 has lines of weakness 350 (the line of weakness on the back panel not being illustrated, it being understood that the line of weakness on the back panel is parallel to the line of weakness on the front panel) that extends adjacent one of the side edges 332 in a generally crooked pattern, e.g., a non-straight pattern and more suitably a wave pattern. FIG. 9 illustrates a fifth embodiment in which the wrapper 420 has straight lines of weakness 450 (only the line of weakness in the front panel being illustrated, it being understood that the line of weakness in the back panel is parallel to the line of weakness in the front panel) that extends in a direction skewed or oblique relative to the longitudinal side edge 432 of the wrapper.

Figure 11:
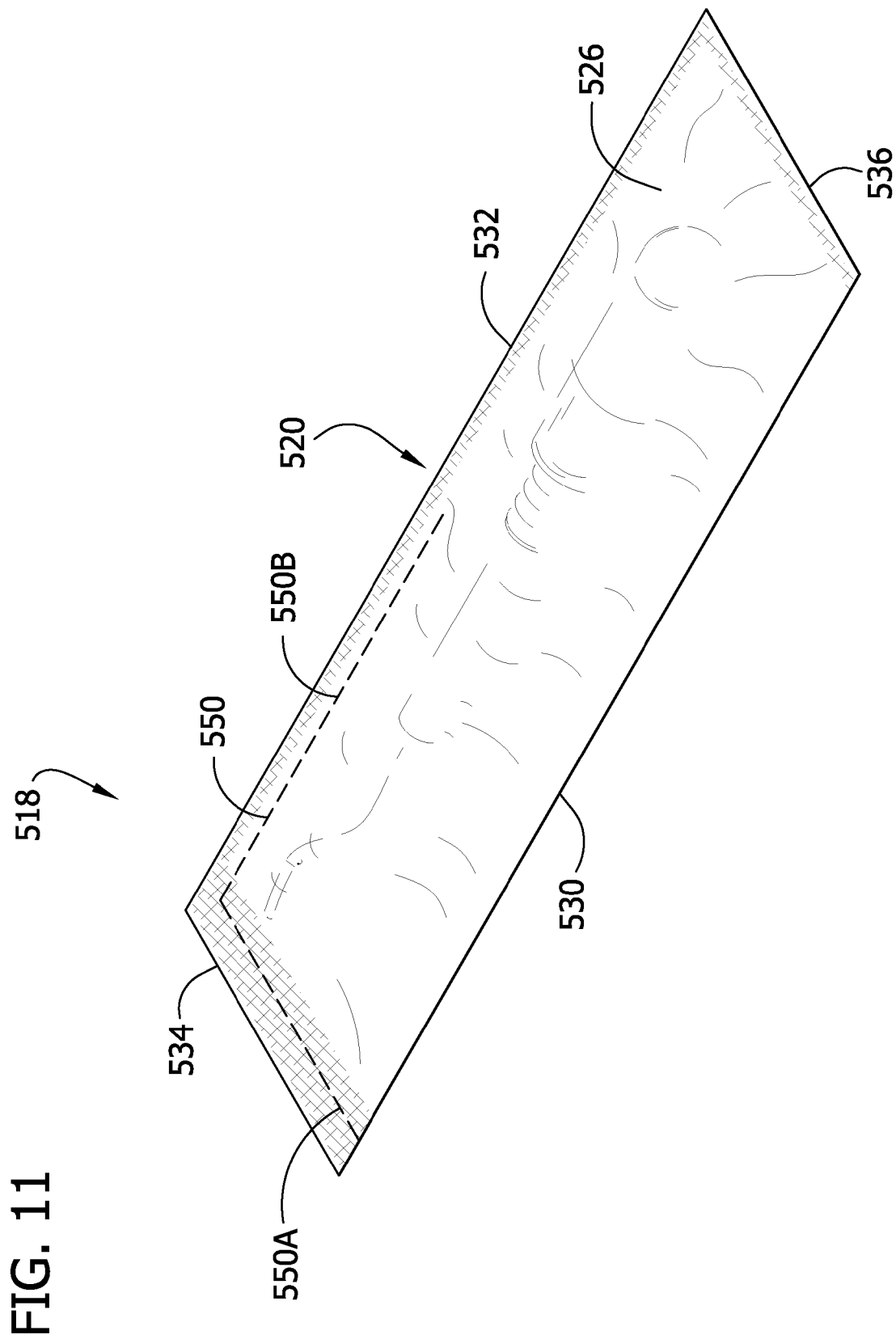
FIG. 11 is a seventh embodiment of a wrapper for a packaged tampon and applicator.

In a seventh embodiment, illustrated in FIG. 11, a wrapper 520 includes a front panel 526, a back panel 528, two side edges 530, 532 and two end edges 534, 536. The front and back panels 526, 528 are joined along one of the side edges 532 and along the end edges 534, 536, such as by heat sealing. A first line of weakness 550 is formed on the front panel 526 of the wrapper and a second line of weakness (not shown) is formed on the back panel 528 of the wrapper. The first and second lines of weakness are, in this embodiment, substantially the same. Accordingly, only the first line of weakness 550 is shown and described. The line of weakness 550 includes a transverse component 550A (i.e., the portion of the line of weakness adjacent the end edge 534) and a longitudinal component 550B (i.e., the portion of the line of weakness adjacent the side edge 532). The longitudinal component 550B is disposed on the wrapper inward of the seal along side edge 532 and has a length that is suitably less than the length of the wrapper 520. The transverse component 550A, on the other hand, extends through the seal along the end edge 534. As a result, the transverse component 550A of the line of weakness 550 has greater rupture strength than the longitudinal component 550B. In other words, a greater force is required to tear the transverse component 550A than the longitudinal component 550B. Thus, the wrapper 550 is inhibited against unintentional tearing along the transverse component.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above products without departing from the scope of the invention, it is intended that all matter contained in the above description and shown in the accompanying drawings shall be interpreted as illustrative and not in a limiting sense.

What is claimed is:

1. A package comprising:
   a tampon and applicator assembly comprising a tampon and an applicator assembled together with the tampon and adapted to facilitate insertion of the tampon in a user; and
   a wrapper for enclosing the tampon and applicator assembly, the wrapper being selectively configurable between a sealed configuration wherein the tampon and applicator assembly are sealingly enclosed in the wrapper and an opened configuration for allowing the tampon and applicator assembly to be removed from the wrapper, the wrapper having a front panel, a back panel, two side edges, two end edges, an interior space, a longitudinal axis, and a transverse axis,
   the front panel having, in the opened configuration of the wrapper, a pair of spaced-apart longitudinal components extending generally parallel to each other and longitudinally of the wrapper to define an opening in the wrapper, each of the longitudinal components being spaced inward from the respective side edge.

2. The package as set forth in claim 1 wherein the wrapper, in the opened configuration, defines a pocket sized for receiving the entire applicator therein following use of the applicator to insert the tampon in the user.

3. The package as set forth in claim 1 wherein the front panel, in the opened configuration of the wrapper, further comprises a transverse component extending transversely of the wrapper.

4. The package set forth in claim 1 wherein the back panel has, in the opened configuration of the wrapper, a pair of spaced-apart longitudinal components extending generally parallel to each other and longitudinally of the wrapper, each of the longitudinal components on the back panel being generally aligned with one of the longitudinal components on the front panel.

5. The package set forth in claim 1 wherein the wrapper has a length and the longitudinal components have length between 20 percent and 75 percent the length of the wrapper.

6. The package set forth in claim 1 wherein the tampon and applicator assembly extend longitudinally within the wrapper.

7. The package set forth in claim 1 wherein the front and back panels are sealed together along the two end edges and one of the side edges.

8. A package comprising:
   a tampon and applicator assembly comprising a tampon and an applicator assembled together with the tampon and adapted to facilitate insertion of the tampon in a user, the applicator including a gripping portion and an insertion portion; and
   a wrapper for enclosing the tampon and applicator assembly, the wrapper being selectively configurable between a sealed configuration wherein the tampon and applicator assembly are sealingly enclosed in the wrapper and an opened configuration for allowing the tampon and applicator assembly to be removed from the wrapper, the wrapper having a front panel, a back panel, two side edges, two end edges, an interior space, a longitudinal axis, and a transverse axis, the front panel, in the opened configuration of the wrapper, having an opening therein for exposing the gripping portion of the applicator, the insertion portion of the applicator being unexposed in the opened configuration of the wrapper until the user removes the tampon and applicator assembly from the wrapper, the opening extending less than a full length of the wrapper such that the wrapper remains a single piece in the opened configuration of the wrapper.

9. A package comprising:
   a tampon and applicator assembly comprising a tampon and an applicator assembled together with the tampon and adapted to facilitate insertion of the tampon in a user, the applicator including a gripping portion and an insertion portion; and
   a wrapper for enclosing the tampon and applicator assembly, the wrapper being selectively configurable between a sealed configuration wherein the tampon and applicator assembly are sealingly enclosed in the wrapper and an opened configuration for allowing the tampon and applicator assembly to be removed from the wrapper, the wrapper having a front panel, a back panel, two side edges, two end edges, an interior space, a longitudinal axis, and a transverse axis, the front panel, in the opened configuration of the wrapper, having an opening therein for exposing the gripping portion of the applicator, the insertion portion of the applicator being unexposed in the opened configuration of the wrapper until the user removes the tampon and applicator assembly from the wrapper, the front panel having, in the opened configuration of the wrapper, a pair of spaced-apart longitudinal components extending generally parallel to each other and longitudinally of the wrapper, each of the longitudinal components being spaced inward from the respective side edge.

10. The package as set forth in claim 9 wherein the front panel, in the opened configuration of the wrapper, further comprises a transverse component extending transversely of the wrapper.

11. The package as set forth in claim 9 wherein the back panel has, in the opened configuration of the wrapper, a pair of spaced-apart longitudinal components extending generally parallel to each other and longitudinally of the wrapper, each of the longitudinal components on the back panel being generally aligned with one of the longitudinal components on the front panel.

12. The package as set forth in claim 8 wherein the wrapper comprises a single-piece of sheet material.

13. The package as set forth in claim 12 wherein one of the side edges is defined by folding the sheet material, the other side edge and each of the end edges being formed by sealing the front and back panels together.

14. The package as set forth in claim 12 wherein the sheet material is a polyethylene film.

15. A package comprising:
   a tampon and applicator assembly comprising a tampon and an applicator assembled together with the tampon and adapted to facilitate insertion of the tampon in a user; and
   a wrapper for enclosing the tampon and applicator assembly, the wrapper being selectively configurable between a sealed configuration wherein the tampon and applicator assembly are sealingly enclosed in the wrapper and an opened configuration for allowing the tampon and applicator assembly to be removed from the wrapper, the wrapper having a front panel, a back panel, two side edges, two end edges, an interior space, a longitudinal axis, and a transverse axis,
   the front panel having, in the opened configuration of the wrapper, a longitudinal component extending longitudinally of the wrapper and a transverse component extending transversely of the wrapper, the longitudinal and transverse components defining an opening in the wrapper, the longitudinal component being spaced inward from the side edges and the transverse component being spaced inward from the end edges.

16. The package as set forth in claim 15 wherein the applicator includes a gripping portion and an insertion portion, the opening in the wrapper being sized and shaped to expose the gripping portion of the applicator, in the opened configuration of the wrapper, while allowing the insertion portion to be unexposed until the user removes the tampon and applicator assembly from the wrapper.

17. The package as set forth in claim 15 wherein the transverse component is a first transverse component and the front panel further comprises a second transverse component spaced from and generally parallel to the first transverse component.

18. The package as set forth in claim 15 wherein the back panel, in the opened configuration, comprises a longitudinal component extending longitudinally of the wrapper and a transverse component extending transversely of the wrapper, the longitudinal and transverse components of the back panel being generally aligned with the longitudinal and transverse components of the front panel.

19. The package as set forth in claim 15 wherein the front panel comprises, in the closed configuration of the wrapper, a line of weakness having a longitudinal component and a transverse component, the longitudinal and transverse components of the line of weakness corresponding to the longitudinal and transverse components defining the opening in the opened configuration of the wrapper.

20. The package as set forth in claim 19 wherein the lines of weakness comprises perforations.

* * * * *